United States Patent [19]

Walker et al.

[11] 4,404,142

[45] Sep. 13, 1983

[54] PREPARATION OF CORTICOIDS FROM 17-KETO STEROIDS

[75] Inventors: Jerry A. Walker, Oshtemo Township, Kalamazoo County; Edward J. Hessler, Kalamazoo, both of Mich.

[73] Assignee: The Upjohn Company, Kalamazoo, Mich.

[21] Appl. No.: 378,940

[22] Filed: May 17, 1982

Related U.S. Application Data

[62] Division of Ser. No. 264,593, May 18, 1981, Pat. No. 4,357,279.

[51] Int. Cl.³ ............................................. C07J 5/00
[52] U.S. Cl. ........................... 260/397.45; 260/239.5; 260/397.5
[58] Field of Search ................................. 260/397.45

[56] References Cited

U.S. PATENT DOCUMENTS

| | | | |
|---|---|---|---|
| 4,041,055 | 8/1977 | Shephard et al. | 260/397.3 |
| 4,336,200 | 6/1982 | Ayer et al. | 260/397.45 |
| 4,342,702 | 8/1982 | Walker | 260/397.45 |

OTHER PUBLICATIONS

J. Am. Chem. Soc. 86, 3840 (1964).
J. Org. Chem. 35, 2831 (1970).

*Primary Examiner*—Elbert L. Roberts
*Attorney, Agent, or Firm*—Bruce Stein

[57] ABSTRACT

A process for the preparation of corticoids (XI) which comprises reacting a protected 17-keto steroid (II) with a metallated 1,2-dihaloethene (III).

39 Claims, No Drawings

PREPARATION OF CORTICOIDS FROM 17-KETO STEROIDS

This application is a division of Ser. No. 264,593, 5-18-81 now U.S. Pat. No. 4,357,279.

BACKGROUND OF THE INVENTION

The present invention relates to an intermediate and processes for preparation of that and other intermediates useful in the preparation of pharmaceutically useful corticoids for which the essential material consituting a disclosure thereof is incorporated here by reference from U.S. patent application Ser. No. 264,593, filed May 18, 1981, now U.S. Pat. No. 4,357,279.

In the past few years, 17-keto steroids have become much more readily available as starting materials for corticoid synthesis because of the discovery of a number of microorganisms which will cleave the $C_{17}$ side chain of various steroid substrates, see U.S. Pat. Nos. 4,035,236, 3,684,657 and 3,759,791.

U.S. Pat. No. 4,041,055 claims a process for producing a 17α-hydroxyprogesterone and corticoids from 17-keto steroids. The first step is addition of a 2-carbon moiety by formation of ethisterone. This is followed (1) by reaction with phenylsulfenyl chloride to form an allene sulfoxide, (2) Michael addition to form a sulfoxide, (3) reaction with a thiophile and (4) reaction with a peracid to give the 17α,21-dihydroxy-20-keto corticoid side-chain.

U.S. Pat. No. 4,216,159 claims a process of transforming a 17-keto steroid to the corresponding 16-unsaturated-21-hydroxy-20-keto steroid by reaction with a lithiated chlorovinyl ether. The objective of that patent is to produce $\Delta^{16}$-$C_{21}$ steroids which can then be used to make $C_{16}$ functionalized corticoids.

The process of the present invention does not involve lithiated chloro vinyl ethers and does not produce $\Delta^{16}$-$C_{21}$ steroids.

The process of the present invention is similar to the process of U.S. Pat. No. 4,041,055 in that it transforms a 17-keto steroid to the corresponding corticoid, but does so by a different synthetic pathway.

the base catalyzed isomerization of β, γ to α,β-unsaturated sulfoxides is well known, see J. Am. Chem. Soc. 86, 3840 (1964) and the addition of nucleophiles to β-halo-α,β-unsaturated sulfoxides has been previously observed in simple systems, see J. Org. Chem. 35, 2831 (1970).

We claim:
1. A 20-substituted steroid of the formula

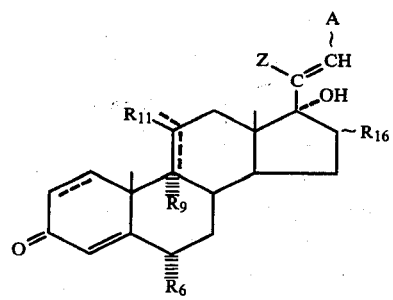

where
A is a fluorine, chlorine, or bromine atom,
$R_6$ is a hydrogen or fluorine atom or methyl group,
$R_9$ is a hydrogen or fluorine atom, hydroxyl group, —OSi(R)$_3$ or nothing,
$R_{11}$ is (H); (H,H); (H, β-OH); (H, β-OSi(R)$_3$); or O,
$R_{16}$ is a hydrogen atom or methyl group,
Z is —OR$_{20}$ or —SR$_{20}$,
~ indicates the attached group can be either the α or β configuration, and
... is a single or double bond.

2. A 20-unsaturated steroid according to claim 1 where A is a chlorine atom.

3. A 20-unsaturated sterod according to claim 1 where Z is methoxy or phenoxy.

4. A 20-unsaturated steroid according to claim 1 where $R_6$ and $R_{16}$ are hydrogen atoms, where $R_9$ is nothing and $R_{11}$ is [H] which gives a $\Delta^{9,11}$ functionality in the C ring.

5. A 20-unsaturated steroid according to claim 4 which is 21-chloro-17α-hydroxy-20-methoxypregna-4,9(11),20(21)-trien-3-one.

6. A process for the preparation of a 20-unsaturated steroid of the formula

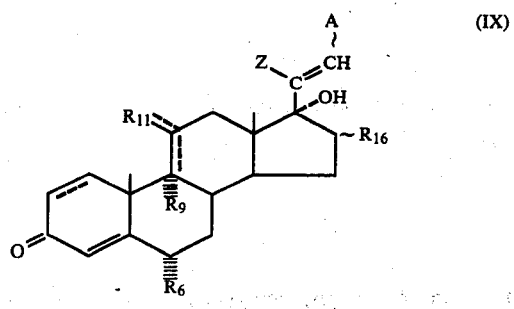

which comprises
(1) contacting a protected 17-keto steroid selected from the group consisting of compounds of the formula

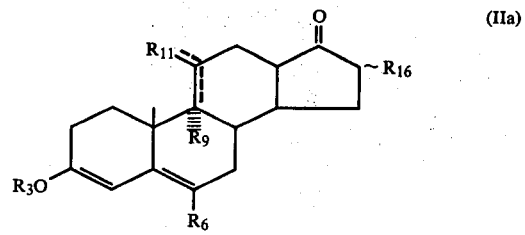

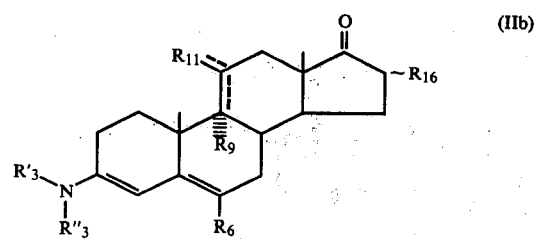

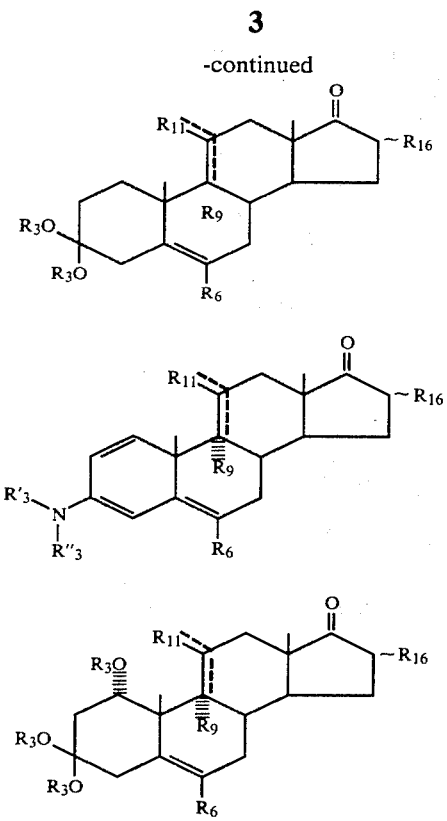

with a metallated 1,2-dihalogenated ethene of the formula

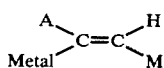  (III)

to form the corresponding protected $C_{21}$-steroid selected from the group consisting of compounds of the formula

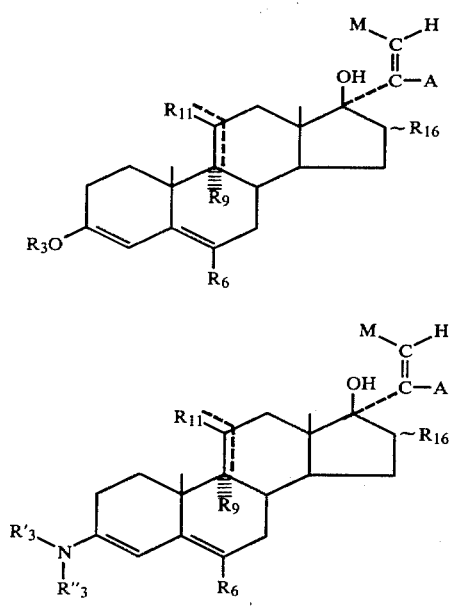

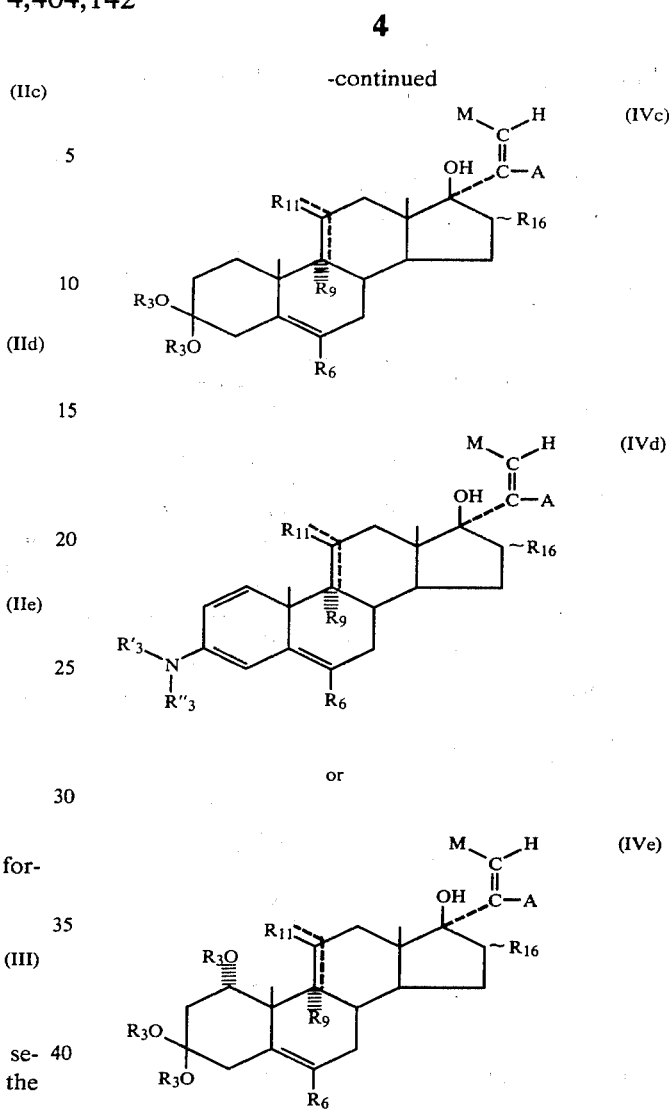

respectively (2) hydrolyzing the protected $C_{21}$-steroids (IVa-IVe) with acid to remove the protecting group and give a $C_{21}$-steroid of the formula (3) contacting the $C_{21}$-steroid (V) with a sulfenylating agent of the formula $R_{22}$-S-X (VI) to give a 20,21-dihalo steroid of the formula

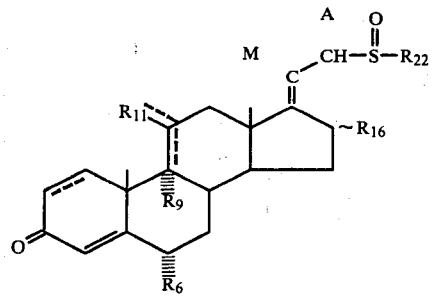

(4) contacting the 20,21-dihalo steroid (VII) with an alkoxide or mercaptide of the formula $OR_{20}^\ominus$, or $SR_{20}^\ominus$, respectively, to give a sulfoxide of the formula

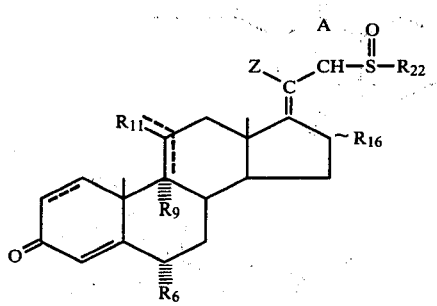

and (5) contacting the sulfoxide (VIII) with a thiophile where

M is a fluorine, chlorine or bromine atom, $R_3$ is alkyl of 1 through 5 carbon atoms with the proviso that with the ketal (IIIc and IIIe), the $R_3$ groups can be connected to form the ethylene ketal, $R_3'$ is alkyl of 1 through 5 carbon atoms, $R_3''$ is alkyl of 1 through 5 carbon atoms, $R_{20}$ is alkyl of 1 through 4 carbon atoms or phenyl, $R_{22}$ is alkyl of 1 through 5 carbon atoms, trichloromethyl, phenyl, phenyl substituted with 1–4 carbon atoms or substituted with 1 through 3 nitro or trifluoromethyl groups, aralkyl of 7 through 12 carbon atoms or $-N-(R_{122})_2$ or phthalimide, X is a chlorine or bromine atom, phenylsulfone, phthalimide or imidazole group, Metal is lithium, sodium or potassium, and where A, $R_6$, $R_9$, $R_{11}$, $R_{16}$, Z, $\sim$ and . . . are defined in claim 1.

7. A process according to claim 6, where for the 20-unsaturated steroid (IX), $R_6$ and $R_{16}$ are hydrogen atoms, where $R_9$ is nothing and $R_{11}$ is [H] which gives a $\Delta^{9,11}$ functionality in the C ring.

8. A process according to claim 6, where the temperature for the coupling reaction is from about $-120$ to about $-20°$.

9. A process according to claim 6, where the coupling reaction is performed in a dry solvent.

10. A process according to claim 6, where the metallated 1,2-dihalogenated ethene (III) is selected from the group consisting of lithiated trans-1,2-dichloroethene, lithiated trans-1,2-chlorofluoroethene, lithiated trans-1,2-dibromoethene, lithiated trans-1,2-difluoroethene and lithiated trans-1,2-bromofluoroethene.

11. A process according to claim 10 where the metallated 1,2-dihalogenated ethene (III) is lithiated trans-1,2-dichloroethene.

12. A process according to claim 6, where the acid to remove the $C_3$ protecting group is present in a catalytic amount.

13. A process according to claim 6, where the acid to remove the $C_3$ protecting group is selected from the group consisting of p-TSA, hydrochloric acid, sulfuric acid, and phosphoric acid.

14. A process according to claim 6 where for the sulfenylating agent, $R_{22}$-S-X, X is a chlorine or bromine atom, and $R_{22}$ is a phenyl group.

15. A process according to claim 6 where the temperature range for the sulfenylating reaction is from about $-80°$ to about $25°$.

16. A process according to claim 6, where the base is an alkoxide.

17. A process according to claim 16, where the alkoxide is methoxide or phenoxide.

18. A process according to claim 6, where the reaction with base is performed in a polar solvent.

19. A process according to claim 6, where 1.5–2.0 equivalents of base are used.

20. A process according to claim 6 where the thiophile is selected from the group consisting of acetone, 3-pentanone, cyclohexanone, 1-(phenylthio)acetone, 2,4-pentanedione, trimethylphosphite, mesityl oxide, dimethyl malonate, 2,6-di-t-butylphenol, ethylvinyl ether, and dihydropyran.

21. A process according to claim 6 where the thiophile is a ketone.

22. A process according to claim 21 where the ketone is acetone.

23. A process for the preparation of a $C_{21}$-steroid of the formula

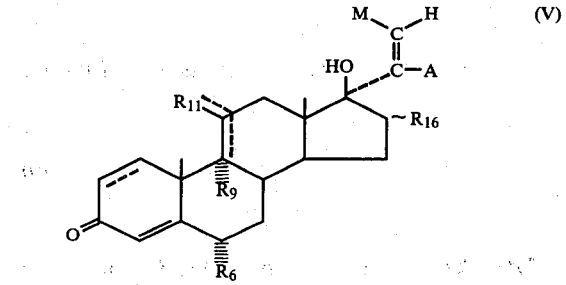

which comprises (1) contacting a protected 17-keto steroid selected from the group consisting of compounds of the formula

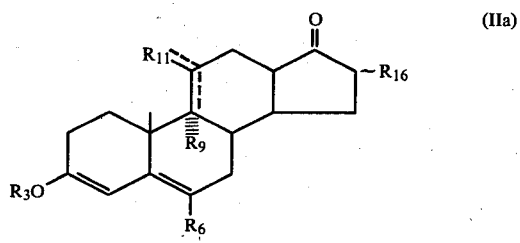

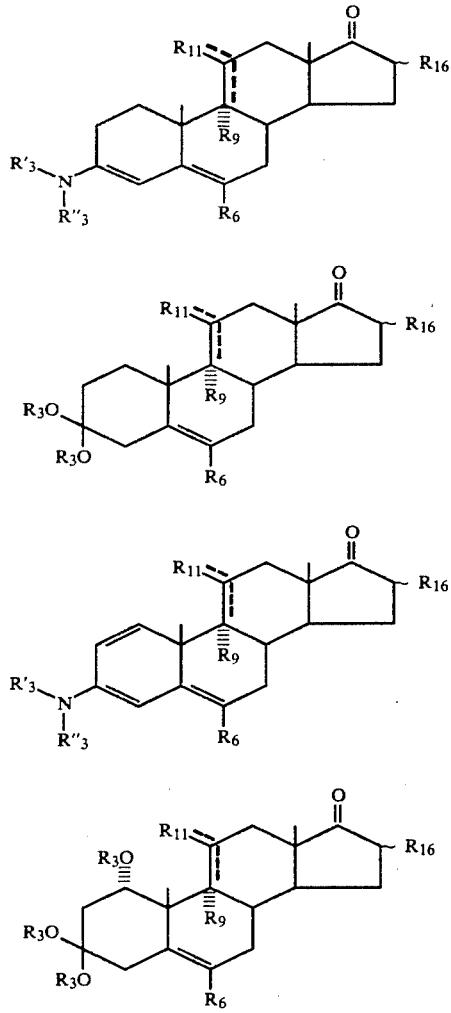

with a metallated 1,2-dihalogenated ethene of the formula

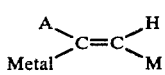

to form the corresponding protected $C_{21}$-steroid selected from the group consisting of compounds of the formula

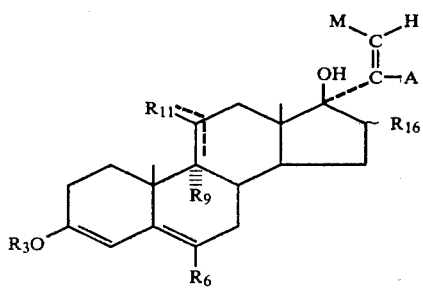

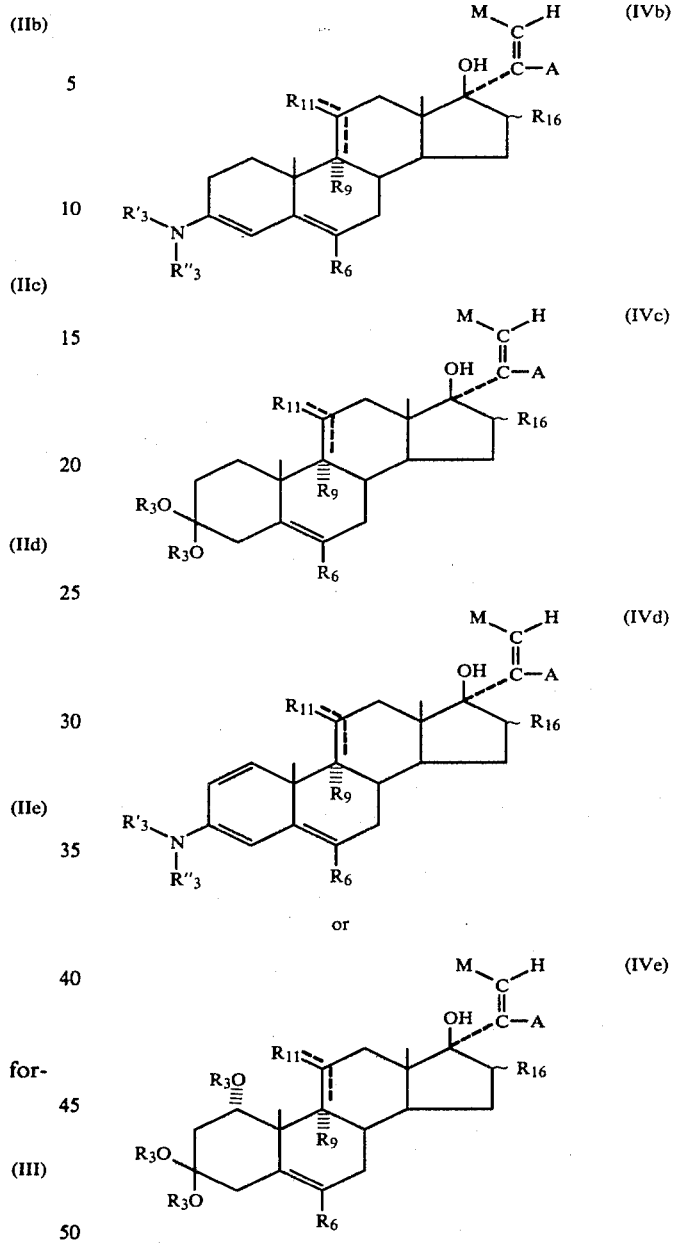

respectively;

(2) hydrolyzing the protected $C_{21}$-steroid (IVa–IVe) to remove the protecting group where A, $R_6$, $R_9$, $R_{11}$, $R_{16}$, ~, and . . . are defined in claim 1, and where M, $R_3$, $R_3'$, $R_3''$ and metal are defined in claim 6.

24. A process according to claim 23, where for the $C_{21}$-steroid (V), $R_6$ and $R_{16}$ are hydrogen atoms, where $R_9$ is nothing and $R_{11}$ is [H] which gives a $\Delta^{9,11}$ functionality in the C ring.

25. A process according to claim 23, where the temperature for the coupling reaction is from about $-120°$ to about $-20°$.

26. A process according to claim 23, where the coupling reaction is performed in a dry solvent.

27. A process according to claim 23, where the metallated 1,2-dihalogenated ethane (III) is selected from the group consisting of lithiated trans-1,2-dichloroethene, lithiated trans-1,2-chlorofluoroethene, lithiated trans-1,2-dibromoethene, lithiated trans-1,2-difluoroethene and lithiated trans-1,2-bromofluoroethene.

28. A process according to claim 27 where the metallated 1,2-dihalogenated ethene (III) is lithiated trans-1,2-dichloroethene.

29. A process according to claim 23, where the acid to remove the $C_3$ protecting group is present in a catalytic amount.

30. A process according to claim 23, where the acid to remove the $C_3$ protecting group is selected from the group consisting of p-TSA, hydrochloric acid, sulfuric acid, and phosphoric acid.

31. A process for the preparation of a 20-unsaturated steroid of the formula

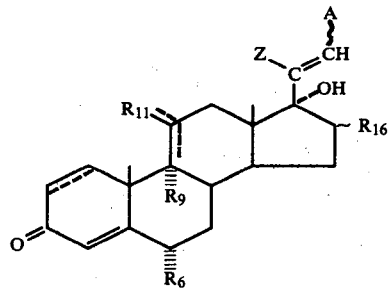
(IX)

which comprises (1) contacting a 20,21-dihalo steroid of the formula

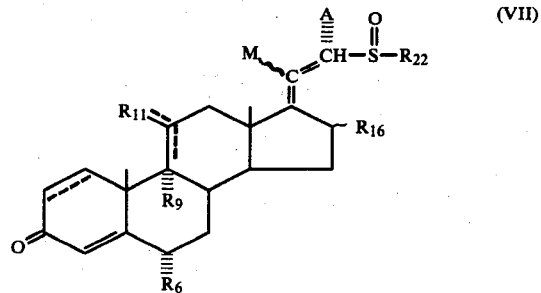
(VII)

with an alkoxide or mercaptide of the formula $OR_{20}^{\ominus}$ or $SR_{20}^{\ominus}$, respectively, to give a sulfoxide of the formula

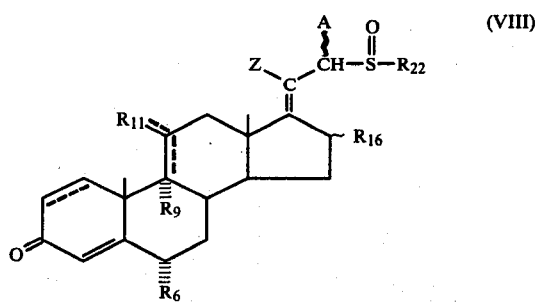
(VIII)

(2) contacting the sulfoxide (VIII) with a thiophile where A, $R_6$, $R_9$, $R_{11}$, $R_{16}$, Z, ~, and ... are defined in claim 1, where M, $R_{20}$ and $R_{22}$ are defined in claim 6.

32. A process according to claim 31, where for the 20-unsaturated steroid (IX), $R_6$ $R_{16}$ are hydrogen atoms, where $R_9$ is nothing and $R_{11}$ is [H] which gives a $\Delta^{9,11}$ functionality in the C ring.

33. A process according to claim 31, where the base is an alkoxide.

34. A process according to claim 33, where the alkoxide is methoxide or phenoxide.

35. A process according to claim 31, where the reaction with base is performed in a polar solvent.

36. A process according to claim 31, where 1.5-2.0 equivalents of base are used.

37. A process according to claim 31, where the thiophile is selected from the group consisting of acetone, 3-pentanone, cyclohexanone, 1-(phenylthio)acetone, 2,4-pentanedione, trimethylphosphite, mesityl oxide, dimethyl malonate, 2,6-di-t-butylphenol, ethylvinyl ether, and dihydropyran.

38. A process according to claim 31, where the thiophile is a ketone.

39. A process according to claim 38, where the ketone is acetone.

* * * * *

UNITED STATES PATENT OFFICE
CERTIFICATE OF CORRECTION

Patent No. 4,404,142              Dated    September 13, 1983

Inventor(s)  Jerry A. Walker et al.

It is certified that error appears in the above-identified patent and that said Letters Patent are hereby corrected as shown below:

Column 2, line 35; and column 9, line 45, in formula (IX) the side chain at $C_{17}$ should appear as follows:

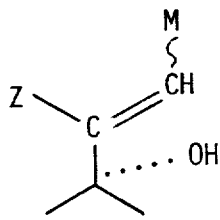

Column 5, line 5 and column 10, line 5, in formula (VII) the side chain at $C_{17}$ should appear as follows:

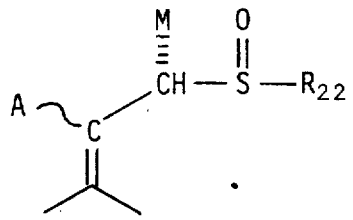

UNITED STATES PATENT OFFICE
CERTIFICATE OF CORRECTION

Patent No. 4,404,142　　　　Dated September 13, 1983

Inventor(s) Jerry A. Walker et al.

It is certified that error appears in the above-identified patent and that said Letters Patent are hereby corrected as shown below:

Column 5, line 25 and column 10, line 25, in formula (VIII) the side chain at $C_{17}$ should appear as follows:

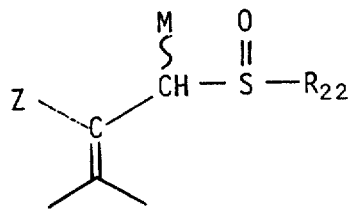

Column 1, line 67 should read --M is a fluorine, chlorine or bromine atom

Signed and Sealed this

Fourth Day of December 1984

[SEAL]

Attest:

Attesting Officer

GERALD J. MOSSINGHOFF

Commissioner of Patents and Trademarks